(12) United States Patent
Pigamo et al.

(10) Patent No.: US 9,061,956 B2
(45) Date of Patent: Jun. 23, 2015

(54) METHOD FOR MANUFACTURING 2,3,3,3-TETRAFLUOROPROPENE

(71) Applicants: Anne Pigamo, Francheville (FR); Nicolas Doucet, Lyons (FR); Laurent Wendlinger, Soucieu en Jarrest (FR)

(72) Inventors: Anne Pigamo, Francheville (FR); Nicolas Doucet, Lyons (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/347,260

(22) PCT Filed: Sep. 20, 2012

(86) PCT No.: PCT/FR2012/052097
§ 371 (c)(1),
(2) Date: Mar. 26, 2014

(87) PCT Pub. No.: WO2013/045791
PCT Pub. Date: Apr. 4, 2013

(65) Prior Publication Data
US 2014/0275653 A1    Sep. 18, 2014

(30) Foreign Application Priority Data

Sep. 27, 2011  (FR) ...................................... 11 58604

(51) Int. Cl.
*C07C 17/20*          (2006.01)
(52) U.S. Cl.
CPC .................................. *C07C 17/206* (2013.01)

(58) Field of Classification Search
USPC ......................................................... 570/160
See application file for complete search history.

(56) References Cited

U.S. PATENT DOCUMENTS

| 2012/0041239 A1* | 2/2012 | Suzuki et al. ................. 570/160 |
| 2012/0330073 A1* | 12/2012 | Karube et al. ................ 570/156 |

FOREIGN PATENT DOCUMENTS

| WO | WO2009/003084 A1 | 6/2007 |
| WO | WO2011/077191 A1 | 12/2009 |
| WO | WO2010/123154 A2 | 4/2010 |

* cited by examiner

*Primary Examiner* — Jafar Parsa
(74) *Attorney, Agent, or Firm* — Brinks Gilson & Lione

(57) ABSTRACT

The present invention relates to a method for manufacturing 2,3,3,3-tetrafluoropropene from halopropanes having the formula $CX_3CHClCH_2X$ and halopropenes having the formulas $CX_3CCl=CH_2$, $CClX_2CCl=CH_2$ and $CX_2=CClCH_2X$, where X is independently a fluorine or chlorine atom. The invention specifically relates to a method including at least one step during which 2-chloro-3,3,3-trifluoro-1-propene, optionally mixed with at least one halopropane having the formula $CX_3CHClCH_2X$ and/or at least one halopropene having the formulas $CClX_2CCl=CH_2$ and $CX_2=CClCH_2X$, where X is independently a fluorine or chlorine atom, reacts with HF in the gaseous phase in the presence of a fluoridation catalyst at a temperature of between 320 and 420° C. with a molar ratio of oxygen to 2-chloro-3,3,3-trifluoro-1-propene of more than 1 but no more than 2.5, and a molar ratio of HF to the total amount of organic compounds to be reacted of between 5 and 40.

16 Claims, No Drawings

METHOD FOR MANUFACTURING 2,3,3,3-TETRAFLUOROPROPENE

This application is a National Stage application of International Application No. PCT/FR2012/052097, filed Sep. 20, 2012. This application also claims priority under 35 U.S.C. §119 to French Application No. 11.58604, filed Sep. 27, 2011.

The present invention relates to a process for manufacturing 2,3,3,3-tetrafluoropropene, which comprises at least one step of fluorination in the gas phase in the presence of a catalyst.

Because of its low Global Warming Potential, 2,3,3,3-tetrafluoropropene (HFO-1234yf) is considered to a potential candidate for replacing HFC-134a in motor vehicle air-conditioning.

2,3,3,3-Tetrafluoropropene can be obtained from 1,2,3,3,3-pentafluoropropene (HFO-1225ye) by reacting HFO-1225ye with hydrogen in the presence of a hydrogenation catalyst so as to give 1,1,1,2,3-pentafluoropropane (HFC-245eb); the HFC-245eb thus formed is then subjected to a step of dehydrofluorination in the presence of potassium hydroxide (Knunyants et al., Journal of Academy of Sciences of the USSR, page 1312-1317, August, 1960).

2,3,3,3-Tetrafluoropropene can also be obtained by reacting 2-chloro-3,3,3-trifluoropropene (HCFO-1233xf) with HF in the presence of a catalyst so as to firstly give 1,1,1,2-tetrafluoro-2-chloropropane (HCFC-244bb), and then the HCFC-244bb reacts with HF on a second catalyst (WO 2007/079431).

2,3,3,3-Tetrafluoropropene can also be obtained from pentachloropropanes or tetrachloropropenes by going through 2-chloro-3,3,3-trifluoropropene as an intermediate.

Document WO 2010123154 describes a process for manufacturing HFO-1234yf by reacting HCFO-1233xf with HF in the presence of oxygen using a chromium oxide catalyst of formula $CrO_m$, with $1.5<m<3$, which is optionally fluorinated. Said document teaches that, in order to obtain good selectivity in terms of HFO-1234yf, the reaction temperature must be between 330 and 380° C. at a pressure of 0.08 to 0.2 MPa with a molar ratio of oxygen to HCFO-1233xf of between 0.1 and 1 and a molar ratio of HF to HCFO-1233xf of between 4 and 30.

Document WO 2010123154 is interested only in the HFO-1234yf selectivity for a very short reaction time (maximum 45 hours). Thus, the conversion is only 6.2% in example 3 after 45 hours of reaction.

However, in order for a process to be industrially viable, not only the selectivity must be high, but also the conversion. In addition, the performance levels must be virtually constant over time.

The applicant has now developed a process for manufacturing 2,3,3,3-tetrafluoropropene which can be carried out industrially and does not exhibit the drawbacks of the prior art. More specifically, the present invention provides a process for manufacturing 2,3,3,3-tetrafluoropropene from halopropanes of formulae $CX_3CHClCH_2X$ and $CX_3CFXCH_3$ and halopropenes of formulae $CX_3CCl=CH_2$, $CClX_2CCl=CH_2$ and $CX_2=CClCH_2X$, where X is independently a fluorine or chlorine atom. The process according to the present invention comprises at least one step (FCO) during which 2-chloro-3,3,3-trifluoro-1-propene, optionally mixed with at least one halopropane of formulae $CX_3CHClCH_2X$ and $CX_3CFXCH_3$ and/or at least one halopropene of formulae $CClX_2CCl=CH_2$ and $CX_2=CClCH_2X$, where X is independently a fluorine or chlorine atom, react(s) with HF in the gas phase in the presence of a fluorination catalyst, at a temperature of between 320 and 420° C., and of a molar ratio of oxygen to 2-chloro-3,3,3-trifluoro-1-propene of greater than 1 and less than or equal to 2.5 and a molar ratio of HF to all the organic compounds to be reacted of between 5 and 40.

The term "organic compounds" is intended to mean compounds comprising at least carbon, chlorine, optionally at least one of the elements chosen from hydrogen and fluorine.

The organic compounds include the starting products and the intermediates.

According to one embodiment, the starting product is chosen from 2,3-dichloro-1,1,1-trifluoropropane (HCFC-243db), 1,1,1,2,3-pentachloropropane (HCC-240db), 2-chloro-3,3,3-trifluoro-1-propene (HCFO-1233xf) and/or 1,1,2,3-tetrachloropropene (HCO-1230xa).

According to one embodiment, the 2-chloro-3,3,3-trifluoro-1-propene represents more than 20% by weight of the organic compound(s) to be reacted with HF in the (FCO) step of the present invention.

According to one preferred embodiment of the invention, the HFO-1234yf is obtained from pentachloropropane, advantageously 1,1,1,2,3-pentachloropropane, and the process comprises an (FCO) step during which the pentachloropropane and/or 2-chloro-3,3,3-trifluoro-1-propene react(s) with HF in the gas phase in the presence of oxygen and of a fluorination catalyst.

Whatever the embodiment, the molar ratio of oxygen to 2-chloro-3,3,3-trifluoro-1-propene to be reacted in the (FCO) step is preferably between 1.25 and 2.5. The molar ratio of HF to all the organic compounds to be reacted in the (FCO) step is preferably between 10 and 40. The fluorination reaction temperature of the (FCO) step is preferably between 340 and 400° C.

The (FCO) step is generally carried out at a pressure of between 0.5 and 20 bar, preferably between 1 and 7 bar.

The catalyst used is a bulk or supported catalyst. The catalyst may be based on a metal, in particular on a transition metal or an oxide, halide or oxyhalide derivative of such a metal. Catalysts are, for example, $FeCl_3$, chromium oxyfluoride, $NiCl_2$, $CrF_3$, and mixtures thereof.

Other possible catalysts are carbon-supported catalysts or catalysts based on magnesium, such as magnesium derivatives, in particular halides such as $MgF_2$ or magnesium oxyhalides such as oxyfluorides, or based on aluminum, such as alumina, activated alumina or aluminum derivatives, in particular halides, such as $AlF_3$, or aluminum oxyhalides such as oxyfluoride.

The catalysts may also comprise co-catalysts chosen from Co, Zn, Mn, Mg, V, Mo, Te, Nb, Sb, Ta, P, Ni, Zr, Ti, Sn, Cu, Pd, Cd, Bi or mixtures thereof. When the catalyst is chromium-based, Ni, Mg and Zn are advantageously chosen as co-catalyst.

The co-catalyst/catalyst atomic ratio is preferably between 0.01 and 5.

Chromium-based catalysts are particularly preferred.

Advantageously, the catalysts are subjected to an activation treatment in the presence of a stream of oxidizing agent, such as air, oxygen or chlorine.

Advantageously, the catalysts are likewise subjected to an activation step using a stream comprising hydrofluoric acid.

According to one embodiment, the activation of the catalysts can be carried out in two steps with a treatment with the oxidizing agent followed by treatment with HF.

According to another embodiment, the activation of the catalysts can be carried out in two steps with a treatment with HF followed by treatment with the oxidizing agent.

Depending on the catalyst or on the reaction, this alternation (activations with an air treatment followed by treatment with HF, again an air treatment followed by treatment with HF, and so on) can be carried out several times.

The temperature of the treatment with the oxidizing agent can be between 250 and 500° C., preferably between 300 and 400° C., for a duration between 10 and 200 hours. The temperature of the treatment with HF can be between 100 and 450° C., preferably between 200 and 300° C., for a duration between 1 and 50 hours.

According to another embodiment, the activation of the catalysts can be carried out in at least one step with a treatment with the mixture of HF and oxidizing agent. The oxidizing agent can represent between 2 and 98 mol % relative to the mixture of HF and oxidizing agent and the activation temperature can range between 200 and 450° C. for a duration between 10 and 200 hours.

The activation of catalyst can be continued by means of a fluorination reaction in the presence of an oxidizing agent, of HF and of at least one compound chosen from a halopropane of formulae $CX_3CHClCH_2X$ and $CX_3CFXCH_3$ and/or at least one halopropene of formulae $CX_3CCl=CH_2$, $CClX_2CCl=CH_2$ and $CX_2=CClCH_2X$, where X is independently a fluorine or chlorine atom. The HF/halopropane and/or halopropene molar ratio can be between 2 and 40. The oxidizing agent/halopropane and/or halopropene molar ratio can be between 0.04 and 2.5. The duration of this step of activation by fluorination can be between 6 and 100 hours and the temperature between 300 and 400° C.

At the end of this activation step, the catalyst is preferably subjected to an air treatment before carrying out the process for manufacturing 2,3,3,3-tetrafluoropropene comprising an (FCO) step according to the present invention.

The activation steps can be carried out at atmospheric pressure or at a pressure of up to 20 bar.

According to one preferred embodiment of the invention, a mixed catalyst containing both chromium and at least one metal chosen from nickel, zinc and magnesium is used. The (Ni/Zn/Mg)Cr atomic ratio is generally between 0.01 and 5.

Advantageously, the catalyst is a mixed chromium and nickel, optionally supported, catalyst.

The metal may be present in metallic form or in the form of derivatives, in particular oxide, halide or oxyhalide, these derivatives, in particular halide and oxyhalide, being obtained by activation of the catalytic metal. Although the activation of the metal is not necessary, it is preferred.

The support is aluminum-based. Mention may be made of several possible supports, such as alumina, activated alumina or aluminum derivatives. These aluminum derivatives are in particular aluminum halides or oxyhalides obtained by means of the activation process described below.

The catalyst may comprise chromium and nickel, magnesium and/or zinc in a non-activated form or in activated form, on a support which has optionally also undergone activation of the metal.

The support can be prepared from alumina with a high porosity. In a first step, the alumina is converted into aluminum fluoride or into a mixture of aluminum fluoride and alumina, by fluorination using air and hydrofluoric acid, the degree of conversion of the alumina to aluminum fluoride essentially depending on the temperature at which the fluorination of the alumina is carried out (in general between 200° C. and 450° C., preferably between 250° C. and 400° C.). The support is then impregnated using aqueous solutions of chromium and nickel, magnesium and/or zinc salts or using aqueous solutions of chromic acid, of nickel, magnesium and/or zinc salt and of methanol (serving as chromium-reducing agent). The chromium and nickel, magnesium and/or zinc salts that may be used include chlorides, or other salts such as, for example, the oxalates, formates, acetates, nitrates and sulfates, or nickel, magnesium and/or zinc bichromate, as long as these salts are soluble in the amount of water that may be absorbed by the support.

The catalyst can also be prepared by direct impregnation of alumina (which in general is activated) using the solutions of the chromium and nickel, magnesium and/or zinc compounds mentioned above. In this case, the conversion of at least part (for example 70% or more) of the alumina into aluminum fluoride or aluminum oxyfluoride is carried out during the step of activation of the metal of the catalyst.

The activated aluminas that may be used for the preparation of the catalyst are well-known commercially available products. They are generally prepared by calcination of alumina hydrates (aluminum hydroxides) at a temperature of between 300° C. and 800° C. The aluminas (activated or nonactivated) can contain large contents (up to 1000 ppm) of sodium, without this harming the catalytic performance.

Preferably, the catalyst is conditioned or activated, i.e. converted into constituents that are active and stable (under the reaction conditions), via a prior "activation" operation. This treatment can be carried out either "in situ" (in the fluorination reactor) or else in a suitable apparatus designed to withstand the activation conditions.

After impregnation of the support, the catalyst is dried at a temperature of between 100° C. and 350° C., preferably 220° C. to 280° C., in the presence of air or nitrogen.

The dried catalyst is then activated in one or two steps with an oxidizing agent and/or hydrofluoric acid. It is then activated by means of a fluorination reaction in the presence of an oxidizing agent, of HF and of at least one compound chosen from a halopropane of formulae $CX_3CHClCH_2X$ and $CX_3CFXCH_3$ and/or at least one halopropene of formulae $CX_3CCl=CH_2$, $CClX_2CCl=CH_2$ and $CX_2=CClCH_2X$, where X is independently a fluorine or chlorine atom. The HF/organic compounds molar ratio can be between 2 and 40. The oxidizing agent/organic compounds molar ratio can be between 0.04 and 2.5. The duration of this step of activation by fluorination can be between 6 and 100 hours and the temperature between 300 and 400° C.

The present invention also provides a process for manufacturing 2,3,3,3-tetrafluoropropene from 2,3-dichloro-1,1,1-trifluoropropane (HCFC-243db), 1,1,1,2,3-pentachloropropane (HCC-240db), 2-chloro-3,3,3-trifluoro-1-propene (HCFO-1233xf) and/or 1,1,2,3-tetrachloropropene (HCO-1230xa) comprising at least one (FCO) step as described above.

The present invention also provides a process for manufacturing 2,3,3,3-tetrafluoropropene by reacting 1,1,1,2,3-pentachloropropane (HCC-240db) with HF in the gas phase in the presence of a catalyst so as to give a stream comprising 2-chloro-3,3,3-trifluoro-1-propene (HCFO-1233xf), HFO-1234yf and optionally 1,1,1,2,2-pentafluoropropane (HFC-245cb); the stream, after separation of the HFO-1234yf, is subjected to an (FCO) step.

The HCC-240db fluorination step and the step for fluorination of the stream, after separation of the HFO-1234yf, can be carried out either in the same reactor or in two separate reactors.

The oxygen present in the (FCO) step can come from air or from oxygen-enriched air.

The process according to the present invention can be carried out continuously or batchwise.

EXPERIMENTAL SECTION

Catalyst

The catalyst used is based on nickel/chromium with an Ni/Cr atomic ratio=1 supported on aluminum fluoride and obtained by impregnation with nickel and chromium salt solutions.

The activation comprises the following steps:

A drying step is carried out at atmospheric pressure under a stream of nitrogen introduced at approximately 20 liter/h and at a temperature of approximately 220° C. for 24 hours;

A first activation step is carried out at a temperature of approximately 350° C. under a mixture of nitrogen and hydrofluoric acid, with the nitrogen being gradually reduced, so as to have a stage under pure HF for 3 hours, and then under a stream of air alone, this being for 64 hours;

A second activation step with air, hydrofluoric acid and HCFO-1233xf: HF/HCFO-1233xf molar ratio=20; oxygen/HCFO-1233xf molar ratio=0.08 and contact time of 25 s, for 30 hours at 350° C.; then a treatment under a stream of air introduced at 1.5 liter/h for 64 hours before carrying out various fluorination reactions.

Chronological scheme of the activation:

Reaction

The fluorination reaction is carried out under the following conditions:

HF/HCFO-1233xf molar ratio=24
oxygen/HCFO-1233xf molar ratio=1.8 or 0.6
contact time=22 s
atmospheric pressure
temperature 350° C.

After 60 hours under these conditions, the HCFO-1233xf conversion is 50% and the selectivity in terms of HFO-1234yf and HFC-245cb is 86%.

After 1690 hours, the conversion is 44% and the selectivity in terms of HFO-1234yf and HFC-245cb is 86%.

The process is carried out as described previously, with the exception that the fluorination reaction is carried out with an HF/HCFO-1233xf ratio=0.6.

After 60 hours under these conditions, the HCFO-1233xf conversion is approximately 32%.

After 250 hours of reaction, the conversion is 28% and the selectivity in terms of HFO-1234yf and HFC-245cb is 88%.

The invention claimed is:

1. A process for manufacturing 2,3,3,3-tetrafluoropropene, comprising reacting 2-chloro-3,3,3-trifluoro-1-propene with HF in the gas phase in the presence of a fluorination catalyst in a reaction vessel at a temperature of between 320 and 420° C., wherein a molar ratio of oxygen to 2-chloro-3,3,3-trifluoro-1-propene in the reaction vessel is greater than 1 and less than or equal to 2.5 and a molar ratio of HF to all of the compounds to be reacted is between 5 and 40.

2. The process of claim 1, wherein 2-chloro-3,3,3-trifluoro-1-propene is mixed with at least one halopropane of formulae $CX_3CHClCH_2X$ and $CX_3CFXCH_3$ and/or at least one halopropene of formulae $CClX_2CCl=CH_2$ and $CX_2=CClCH_2X$, where X is independently a fluorine or chlorine atom.

3. The process as claimed in claim 1, wherein the molar ratio of oxygen to 2-chloro-3,3,3-trifluoro-1-propene is between 1.25 and 2.5.

4. The process as claimed in claim 2, wherein the molar ratio of HF to the organic compounds to be reacted is between 10 and 40.

5. The process as claimed in claim 1, wherein the fluorination temperature is between 340 and 400° C.

6. The process as claimed in claim 1, wherein the reaction is carried out at a pressure of between 0.5 and 20 bar.

7. The process as claimed in claim 2, wherein 2-chloro-3,3,3-trifluoro-1-propene represents at least 20% by weight of organic compound(s) present in the reaction.

8. The process as claimed in claim 1, wherein the catalyst is a bulk or supported catalyst.

9. The process as claimed in claim 1, wherein the catalyst is chromium-based.

10. The process as claimed in claim 1, wherein the catalyst comprises a co-catalyst.

11. The process as claimed in claim 10, wherein the co-catalyst is selected from the group consisting of nickel, magnesium and zinc.

12. The process as claimed in claim 1, further comprising subjecting the catalyst to at least one activation step using a stream comprising oxygen and/or HF.

13. The process as claimed in claim 12, wherein the activation is continued via a fluorination reaction in the presence of an oxidizing agent, HF and at least one compound selected from the group consisting of halopropanes of formulae $CX_3CHClCH_2X$ and $CX_3CFXCH_3$ and halopropenes of formulae $CX_3CCl=CH_2$, $CClX_2CCl=CH_2$ and $CX_2=CClCH_2X$, where X is independently a fluorine or chlorine atom.

14. The process as claimed in claim 13, wherein the temperature is between 300 and 400° C. and the duration between 6 and 100 hours.

15. The process as claimed in claim 2, wherein the halopropanes or halopropenes are selected from the group consisting of 2,3-dichloro-1,1,1-trifluoropropane, 1,1,1,2,3-pentachloropropane, 2-chloro-3,3,3-trifluoro-1-propene and 1,1,2,3-tetrachloropropene.

16. A process for manufacturing 2,3,3,3-tetrafluoropropene comprising reacting 1,1,1,2,3-pentachloropropane with HF in the gas phase in the presence of a catalyst to yield an intermediate stream comprising 2-chloro-3,3,3-trifluoro-1-propene, 2,3,3,3-tetrafluoropropene and, optionally, 1,1,1,2,2-pentafluoropropane;

separating 2,3,3,3-tetrafluoropropene from the intermediate stream to form a second intermediate stream comprising 2-chloro-3,3,3-trifluoro-1-propene and, optionally, 1,1,1,2,2-pentafluoropropane, and reacting the second intermediate stream with HF in the gas phase in the presence of a fluorination catalyst at a temperature of between 320 and 420° C. in a reaction vessel, wherein a molar ratio of oxygen to 2-chloro-3,3,3-trifluoro-1-propene in the reaction vessel is greater than 1 and less than or equal to 2.5 and a molar ratio of HF to all of the compounds to be reacted is between 5 and 40.

* * * * *